(12) United States Patent
Schwab et al.

(10) Patent No.: US 10,982,422 B2
(45) Date of Patent: Apr. 20, 2021

(54) WASH SYSTEM WITH A CLEANSER ASSEMBLY

(71) Applicant: Whole Bath, LLC, East Chatham, NY (US)

(72) Inventors: Brian Schwab, East Chatham, NY (US); Shao-Yu Peng, Changhua County (TW)

(73) Assignee: Whole Bath, LLC, East Chatham, NY (US)

( * ) Notice: Subject to any disclaimer, the term of this patent is extended or adjusted under 35 U.S.C. 154(b) by 0 days.

(21) Appl. No.: 15/674,536

(22) Filed: Aug. 11, 2017

(65) Prior Publication Data

US 2018/0044903 A1    Feb. 15, 2018

Related U.S. Application Data

(60) Provisional application No. 62/373,957, filed on Aug. 11, 2016.

(51) Int. Cl.
| | |
|---|---|
| *E03D 9/08* | (2006.01) |
| *A47K 13/30* | (2006.01) |
| *A47K 10/48* | (2006.01) |
| *B05B 7/32* | (2006.01) |
| *B05B 9/04* | (2006.01) |
| *B05B 13/04* | (2006.01) |
| *B05B 15/70* | (2018.01) |

(52) U.S. Cl.
CPC ............... *E03D 9/08* (2013.01); *A47K 10/48* (2013.01); *A47K 13/302* (2013.01); *B05B 7/32* (2013.01); *B05B 9/0403* (2013.01); *B05B 13/0431* (2013.01); *B05B 15/70* (2018.02)

(58) Field of Classification Search
CPC ........ E03D 9/08; A47K 13/302; A47K 10/48; B05B 7/32; B05B 9/0403; B05B 15/70; B05B 13/0431
See application file for complete search history.

(56) References Cited

U.S. PATENT DOCUMENTS

| | | |
|---|---|---|
| 2,875,450 A | 3/1959 | Umann |
| D198,085 S | 4/1964 | Rich |
| 3,306,252 A | 2/1967 | Knight |
| 3,516,424 A | 6/1970 | Eagle |

(Continued)

FOREIGN PATENT DOCUMENTS

| | | |
|---|---|---|
| CN | 201551648 | 8/2010 |
| CN | 101933781 | 1/2011 |

(Continued)

OTHER PUBLICATIONS

U.S. Appl. No. 15/847,594 dated Dec. 19, 2019, Brian Schwab.

(Continued)

*Primary Examiner* — Janie M Loeppke
(74) *Attorney, Agent, or Firm* — Michael D. Eisenberg (57) ABSTRACT

A method and a wash, clean, dry and protect system are provided for easy handling, for washing, cleansing, drying and/or protecting a body part, and for the delivery of water and/or a cleansing solution to a surface area of a human subject. The built-in cleanser assembly is incorporated onto a wash and clean bidet seat system for washing, cleansing, drying and protecting private body parts of the person.

18 Claims, 8 Drawing Sheets

(56) References Cited

U.S. PATENT DOCUMENTS

| | | | | |
|---|---|---|---|---|
| 3,810,260 A | * | 5/1974 | Lodi | A47K 7/08 4/420.4 |
| 3,995,326 A | | 12/1976 | Umann | |
| 4,279,362 A | | 7/1981 | Pursell | |
| 4,287,618 A | | 9/1981 | Silver | |
| 4,327,560 A | | 5/1982 | Leon et al. | |
| D266,758 S | | 11/1982 | Johannsen | |
| 4,422,189 A | | 12/1983 | Couvrette | |
| D279,184 S | | 6/1985 | Sakamoto | |
| 4,628,548 A | | 12/1986 | Kurosawa | |
| D303,966 S | | 10/1989 | Fritzsche | |
| 4,903,347 A | | 2/1990 | Garcia | |
| 4,987,617 A | | 1/1991 | Furukawa | |
| 5,031,252 A | * | 7/1991 | Oyama | A47K 13/302 4/222 |
| 5,101,520 A | | 4/1992 | Lockhart | |
| 5,201,080 A | * | 4/1993 | Tanaka | E03D 9/08 4/443 |
| 5,203,037 A | | 4/1993 | Kang | |
| 5,247,711 A | | 9/1993 | Kwon | |
| 5,335,855 A | | 8/1994 | Borod | |
| D355,246 S | | 2/1995 | Kawamura | |
| 5,409,167 A | | 4/1995 | Borod | |
| D367,922 S | | 3/1996 | Kobayashi | |
| 5,504,948 A | | 4/1996 | Chandler | |
| 5,551,098 A | | 9/1996 | Wilk | |
| 5,566,402 A | | 10/1996 | Agha El-Rifai | |
| 5,630,234 A | | 5/1997 | Childs | |
| D387,851 S | | 12/1997 | Pieters | |
| 5,720,054 A | | 2/1998 | Nakayama | |
| 5,765,238 A | | 6/1998 | Furukawa | |
| 5,813,060 A | | 9/1998 | Klopocinski | |
| 5,864,894 A | | 2/1999 | Fedele | |
| 5,898,956 A | | 5/1999 | Kurisaki | |
| 5,911,516 A | | 6/1999 | Chang | |
| 5,953,765 A | | 9/1999 | Hayashi | |
| 5,987,659 A | | 11/1999 | Cannizzaro | |
| 6,003,159 A | | 12/1999 | Sadegh | |
| 6,009,570 A | | 1/2000 | Hargest | |
| D423,655 S | | 4/2000 | Otte | |
| 6,073,275 A | | 6/2000 | Klopocinski | |
| 6,105,178 A | | 8/2000 | Kurisaki | |
| D432,220 S | | 10/2000 | Hulsebus | |
| 6,128,788 A | | 10/2000 | Yamazaki | |
| D435,638 S | | 12/2000 | Merry | |
| 6,167,577 B1 | | 1/2001 | Hammad | |
| 6,178,568 B1 | | 1/2001 | Boulieris | |
| 6,192,527 B1 | | 2/2001 | Paul | |
| D451,076 S | | 11/2001 | Sommer | |
| D451,177 S | | 11/2001 | Scholpp | |
| 6,339,852 B1 | | 1/2002 | Huang | |
| 6,397,406 B1 | | 6/2002 | Moshkovich | |
| 6,449,780 B1 | | 9/2002 | Merry | |
| 6,481,590 B1 | | 11/2002 | Simkins | |
| D471,966 S | | 3/2003 | Takahashi | |
| D481,016 S | | 10/2003 | Hillis | |
| D485,337 S | | 1/2004 | Tani | |
| 6,688,500 B1 | | 2/2004 | Cheng | |
| 6,691,328 B2 | * | 2/2004 | Delfino | E03D 9/037 222/56 |
| 6,754,912 B1 | | 6/2004 | Hayashi | |
| D500,130 S | | 12/2004 | Jung | |
| D508,733 S | | 8/2005 | Peng | |
| D512,425 S | | 12/2005 | Nakagawa | |
| 6,973,679 B1 | | 12/2005 | Schad | |
| 7,096,518 B2 | | 8/2006 | Takenaga | |
| D528,991 S | | 9/2006 | Katsuyama | |
| 7,120,946 B1 | | 10/2006 | Lazar | |
| 7,127,750 B2 | | 10/2006 | Lim | |
| D533,788 S | | 12/2006 | Kleiman | |
| 7,155,755 B2 | | 1/2007 | Olivier | |
| D538,907 S | | 3/2007 | Kaule | |
| 7,191,473 B2 | | 3/2007 | Matsumoto | |
| D541,225 S | | 4/2007 | Katsuyama | |
| 7,216,374 B2 | | 5/2007 | Hassan | |
| 7,284,285 B2 | * | 10/2007 | Scalzi | E03D 9/08 4/213 |
| 7,287,286 B2 | | 10/2007 | Lee | |
| D554,613 S | | 11/2007 | Nakatani | |
| D558,181 S | | 12/2007 | Takada | |
| D564,976 S | | 3/2008 | Jackson | |
| D565,554 S | | 4/2008 | Fan | |
| D578,515 S | | 10/2008 | Ikeda et al. | |
| D579,342 S | | 10/2008 | Priestman | |
| D583,030 S | | 12/2008 | Kobayashi | |
| D594,537 S | | 6/2009 | Driedger | |
| D594,945 S | | 6/2009 | Nakasaki et al. | |
| 7,543,339 B1 | * | 6/2009 | Harris | E03D 1/01 4/420.5 |
| D608,426 S | | 1/2010 | Watanabe | |
| D616,445 S | | 5/2010 | Wong et al. | |
| D634,735 S | | 3/2011 | Maier | |
| D639,399 S | | 6/2011 | Takeuchi | |
| D639,400 S | | 6/2011 | Kang | |
| 7,954,181 B2 | | 6/2011 | Lim | |
| 8,060,953 B1 | | 11/2011 | Dorra | |
| D654,808 S | | 2/2012 | Gidlow | |
| 8,161,580 B2 | | 4/2012 | Hashidume | |
| 8,261,377 B2 | | 9/2012 | Oh | |
| D668,642 S | | 10/2012 | Feldman et al. | |
| 8,291,527 B2 | | 10/2012 | Pan | |
| D670,659 S | | 11/2012 | Yoshioka | |
| D671,935 S | | 12/2012 | Mao | |
| 8,365,317 B1 | | 2/2013 | Dorra | |
| 8,425,475 B2 | | 4/2013 | Sodo | |
| D682,246 S | | 5/2013 | Boqueho | |
| D688,359 S | | 8/2013 | Ogata et al. | |
| D692,417 S | | 10/2013 | Tu | |
| D692,541 S | | 10/2013 | Hosoi et al. | |
| D698,754 S | | 2/2014 | Vignau-Louis | |
| D703,797 S | | 4/2014 | Shinozaki | |
| D704,316 S | | 5/2014 | Yoshioka | |
| D704,317 S | | 5/2014 | Yoshihiko | |
| D706,402 S | | 6/2014 | Yeung | |
| D708,954 S | | 7/2014 | Barnes | |
| 8,776,278 B1 | | 7/2014 | Dorra | |
| D713,815 S | | 9/2014 | Ookawa | |
| D715,774 S | | 10/2014 | Lee et al. | |
| D716,768 S | | 11/2014 | Kim | |
| D717,930 S | | 11/2014 | Kergoet | |
| 8,904,575 B1 | | 12/2014 | Lindheimer | |
| D724,058 S | | 3/2015 | Chandel | |
| D724,059 S | | 3/2015 | Kim | |
| 9,049,970 B2 | * | 6/2015 | Dorra | A47K 13/302 |
| D750,765 S | | 3/2016 | Giametta | |
| 9,273,454 B2 | | 3/2016 | Slawinski | |
| 9,279,241 B2 | | 3/2016 | Morioka | |
| D753,095 S | | 4/2016 | Moran | |
| 9,464,425 B2 | | 10/2016 | Bailey | |
| D781,808 S | | 3/2017 | Pista | |
| D792,867 S | | 7/2017 | Murphy | |
| D805,615 S | | 12/2017 | Peng | |
| 9,889,982 B2 | | 2/2018 | Falcon | |
| 2003/0140407 A1 | | 7/2003 | Matsumoto | |
| 2004/0055080 A1 | | 3/2004 | Marshall | |
| 2005/0000006 A1 | | 1/2005 | Takenaga | |
| 2005/0010997 A1 | | 1/2005 | Olivier | |
| 2006/0000012 A1 | | 1/2006 | Schad | |
| 2006/0047055 A1 | | 3/2006 | Agostini | |
| 2006/0265801 A1 | | 11/2006 | Riccobon | |
| 2007/0241929 A1 | | 10/2007 | Marchetto | |
| 2008/0055394 A1 | | 3/2008 | Shiue | |
| 2008/0201837 A1 | | 8/2008 | Oh | |
| 2008/0251551 A1 | | 10/2008 | Huber | |
| 2009/0313752 A1 | | 12/2009 | Kunimoto | |
| 2010/0012685 A1 | | 1/2010 | Ramsey | |
| 2010/0152475 A1 | | 6/2010 | Raichle | |
| 2010/0176224 A1 | | 7/2010 | Hasselschwert | |
| 2011/0132929 A1 | | 6/2011 | Bennett | |
| 2011/0133001 A1 | | 6/2011 | Cooper | |
| 2011/0191950 A1 | | 8/2011 | Liu | |
| 2011/0203044 A1 | | 8/2011 | Lim | |
| 2012/0005817 A1 | | 1/2012 | Jeong | |
| 2012/0011647 A1 | | 1/2012 | Mochita | |

(56) References Cited

U.S. PATENT DOCUMENTS

| | | |
|---|---|---|
| 2012/0150148 A1 | 6/2012 | Shi |
| 2012/0180785 A1 | 7/2012 | Trill |
| 2012/0266483 A1 | 10/2012 | Palermo et al. |
| 2013/0133131 A1 | 5/2013 | Peng |
| 2013/0180041 A1 | 7/2013 | Ding |
| 2013/0267890 A1 | 10/2013 | Li |
| 2014/0042195 A1 | 2/2014 | Geis |
| 2014/0047626 A1 | 2/2014 | Dorra |
| 2014/0068862 A1 | 3/2014 | Al-Jafar |
| 2014/0107409 A1 | 4/2014 | Bailey et al. |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2016/0316978 A1 | 11/2016 | Peng |
| 2017/0021116 A1 | 1/2017 | Rahmel |
| 2017/0101838 A1 | 4/2017 | Razvi |
| 2017/0142306 A1 | 5/2017 | Peng |
| 2017/0265624 A1 | 9/2017 | Wilson |
| 2017/0319794 A1 | 11/2017 | Schwab |
| 2017/0321406 A1 | 11/2017 | Schwab |
| 2017/0321407 A1 | 11/2017 | Schwab |
| 2017/0321408 A1 | 11/2017 | Schwab |
| 2018/0015238 A1 | 1/2018 | Schwab |
| 2018/0028797 A1 | 2/2018 | Schwab |
| 2018/0036473 A1 | 2/2018 | Schwab |

FOREIGN PATENT DOCUMENTS

| | | |
|---|---|---|
| DE | 1625201 | 2/1970 |
| EP | 2138640 | 12/2009 |
| EP | 025022450001 | 7/2014 |
| FR | 2671294 | 7/1992 |
| FR | 2869596 | 11/2005 |
| GB | 2351779 | 1/2001 |
| IN | 2689190001 | 10/2015 |
| JP | S4815806 | 2/1973 |
| JP | H0893034 | 4/1996 |
| JP | H0988165 | 3/1997 |
| JP | H1163666 | 3/1999 |
| JP | 2001279778 | 10/2001 |
| JP | 2003342993 | 12/2003 |
| JP | 2007321443 | 12/2007 |
| JP | 2015206183 | 11/2015 |
| WO | 2008024005 | 2/2008 |
| WO | 2013020240 | 2/2013 |
| WO | WO 2012/044086 A2 | 4/2017 |

OTHER PUBLICATIONS

Final Office Action for U.S. Appl. No. 15/588,640 dated Dec. 3, 2018.

PCT Notification of Transmittal of The International Search Report and The Written Opinion of The International Searching Authority, or Declaration, PCT/US2017/031482, filed on May 6, 2017 by Whole Bath, LLC.

PCT Notification of Transmittal of The International Search Report and The Written Opinion of The International Searching Authority, or Declaration, PCT/US2017/031483, filed on May 6, 2017 by Whole Bath, LLC.

PCT Notification of Transmittal of The International Search Report and The Written Opinion of The International Searching Authority, or Declaration, PCT/US2017/031484, filed on May 6, 2017 by Whole Bath, LLC.

PCT Notification of Transmittal of The International Search Report and The Written Opinion of The International Searching Authority, or Declaration, PCT/US2017/031485, filed on May 6, 2017 by Whole Bath, LLC.

PCT Notification of Transmittal of The International Search Report and The Written Opinion of the International Searching Authority, PCT/US2016/45932, dated Oct. 24, 2016.

PCT Notification of Transmittal of The International Search Report and The Written Opinion of the International Searching Authority, PCT/US2017/042288, dated Sep. 28, 2017.

PCT Notification of Transmittal of The International Search Report and The Written Opinion of The International Searching Authority, PCT/US2017/42253, dated Nov. 21, 2017.

Schwabcare website 2017, http://schwabcare.com/, site visited Jan. 21, 2018.

Kohler, Self-Cleaning Wand, https://www.youtube.com/watch?v=z629hpdnWj8, published Oct. 12, 2016.

Office Action from Chinese Patent Application No. 2017800570280, with English translation, dated Nov. 27, 2019; 22 pages.

Extended European Search Report for European Patent Application No. 17831608.9 dated Feb. 25, 2020.

Extended Euorpean Search Report for European Application No. 17831614 dated Mar. 18, 2020.

* cited by examiner

WASH SYSTEM WITH A CLEANSER ASSEMBLY

CROSS-REFERENCE TO RELATED APPLICATIONS

This application claims benefit of U.S. provisional patent application Ser. No. 62/373,957, filed Aug. 11, 2016, which is herein incorporated by reference.

BACKGROUND OF THE INVENTION

Embodiments of the present invention generally relate to a wash system with built-in cleanser assembly for the delivery of a cleanser solution to a surface area of a human subject. More specifically, aspects of the present invention provide a method and a wash system with a built-in cleanser assembly for washing and applying a cleaning solution to a region of a human body (e.g., skin, genital or anal area, intimate parts, perianal region) and cleaning thereof.

DESCRIPTION OF THE RELATED ART

Bidets and other modern toilet seat systems have been used to spray water and clean private parts of a user using a toilet. The bidet systems are used for washing the genital and anal areas using cleaning water of appropriate temperature sprayed from the center of the bidet system, instead of toilet paper after relief stool or urination. Originally being developed for washing the pubic area for females, bidet systems have now been popular among people of all ages and both sexes because it is known to be more hygienic to wash the intimate parts and anus with water instead of paper after relief. In addition, cleansing the pubic/anal regions with water may help to avoid infection and prevent hemorrhoids and other anal disease. Furthermore, it is very effective for women with gynecological diseases. It is also very useful for the elderly or obese people to relieve themselves with great convenience.

People who have problems controlling their urine or bowels and suffer from incontinence are at risk of skin problems around the buttocks, hips, genitals, and the area between the pelvis and rectum (perineum). Excess moisture in these areas may result in skin problems (e.g., redness, peeling, irritation, and yeast infections, etc.), and if the person spends most of his or her day in a wheelchair, or bed, it is likely that bedsores may also develop. Such skin problems may be worse if the person uses diapers and other products, which allow urine or stool to be in constant contact with the skin. As such, special care by cleaning and drying the area right away after urinating or having a bowel movement, and/or cleaning the skin with mild, dilute soap and water then rinsing well and gently patting dry.

In applying a skin cleanser or soap to an individual's skin, if the individual is alone, this is impossible since an individual cannot adequately apply such skin cleanser fluid onto hard-to-reach areas of his or her own back and bottom. Accordingly, it is necessary to utilize the services of a second individual to apply a skin cleanser fluid on hard-to-reach areas such as the back and upper neck.

Thus, there is a need for using a spray wash system with built-in cleanser assembly to apply a cleanser solution to the skin area of a person, to be incorporated into a bidet seat cleaning systems have water spray nozzle for washing and cleaning private parts of the person.

SUMMARY OF THE INVENTION

The present invention generally provides a method and a wash, clean, dry and protect system that is easy to handle for washing, cleansing, drying, and/or protecting a body part, and for the delivery of water, a cleansing solution, and/or any other suitable solutions to a surface area of a human subject. In one embodiment, a wash system is provided and includes a toilet seat assembly having a seat cover, a seat base, and a base housing within the seat base. In one aspect, the seat cover is adapted to be laid down on top of the seat base in a seat-close position. In another aspect, the seat cover is adapted to be put up over the seat base in a seat-open position.

In one embodiment, a cleanser assembly and a nozzle spray assembly are position inside the base housing of the toilet seat assembly, where the cleanser assembly is adapted to contain one or more cleansers therein. In another embodiment, the nozzle spray assembly is connected to the one or more cleanser containers of the cleanser assembly inside the base housing of the toilet seat assembly. The wash system may further include a dryer assembly.

In one aspect, the wash system includes a top cover positioned on a top portion of the base housing of the seat base. In another aspect, wherein the top cover is adapted to be opened when the seat cover is laid down on top of the seat base in the seat-close position. In another aspect, the top cover is adapted to be opened when the seat cover is put up over the seat base in the seat-open position.

In still another aspect, the wash system further includes a nozzle cover positioned on a side-wall of the base housing of the seat base. In one example, the nozzle cover is adapted to be in an open position ready for one or more nozzles from the nozzle spray assembly to extend out when the seat cover is put up over the seat base in the seat-open position. In one example, the nozzle cover is adapted to be in a closed position.

Another aspect of the invention provides the cleanser assembly having one or more cleanser containers positioned therein and adapted to contain one or more concentrated cleansers. In addition, the cleanser assembly may further include a cleanser port having an opening on a first end and connecting to the one or more cleanser containers on a second end.

In one embodiment, the cleanser assembly further includes a cleanser dosing valve adapted to be connected to the one or more cleanser containers, and a pump positioned to pump a dose of the one or more concentrated cleansers from the cleanser dosing valve to a water port of the nozzle spray assembly, where one or more doses of the one or more cleansers are delivered from the one or more cleanser containers of the cleanser assembly to the nozzle spray assembly to be mixed with water into a cleanser solution.

In another embodiment, the cleanser assembly also includes a sensor being positioned on a surface of the one or more cleanser containers and adapted to detect a level of the one or more cleansers inside the one or more cleanser containers. In another aspect, one or more doses of the one or more cleansers within the one or more cleanser containers are delivered from the cleanser assembly to the nozzle spray assembly to be mixed with water into a cleanser solution. Examples of the one or more cleansers include skin repair creams, skin protectants, skin extra protective creams (EPC), skin lotions, mild soaps, detergents, mild anti-bacterial soaps, and combinations thereof. In one example, the cleansers comprise benzalkonium chloride.

In still another embodiment, the nozzle spray assembly includes a water spray nozzle with a water spray nozzle head and the cleanser solution is sprayed out of the water spray nozzle head. In an alternative embodiment, the nozzle assembly includes a cleanser spray nozzle and a water spray nozzle, and the cleanser solution is sprayed out of a cleanser spray nozzle head of the cleanser spray nozzle.

Another embodiment of the invention provides a method for using a wash system by a human subject. The method includes dosing one or more doses of one or more cleansers contained within a cleanser container of a cleanser assembly to be directed into a nozzle spray assembly of the wash system, and spraying out a cleanser solution from a nozzle head of the nozzle spray assembly of the wash system, where the wash system includes a toilet seat assembly, the cleanser assembly, and the nozzle spray assembly connected to the cleanser container of the cleanser assembly inside a base housing of the toilet seat assembly.

The toilet seat generally includes a seat cover, a seat base, and the base housing within the seat base, where the seat cover is adapted to be laid down on top of the seat base in a seat-close position and/or to be put up over the seat base in a seat-open position. The cleanser assembly is positioned inside the base housing of the toilet seat assembly and is adapted to contain the one or more cleanser containers containing the one or more cleansers therein.

In one aspect, the method also includes opening a top cover of the wash system prior to cleaning a body part of the human body. In addition, the method also includes cleansing a surface area of the body part of the human subject using the cleanser solution being sprayed out of a nozzle head of the nozzle spray assembly, and/or washing the surface area of the human subject using water. In another aspect, the method includes drying the surface area of the human subject using a dryer assembly of the wash system.

In another aspect, the method may also include opening a cap of the cleanser container within the cleanser assembly of the wash system, and pouring a portion of the one or more cleansers from a cleanser bottle into the cleanser container of the cleanser assembly. Further, the method includes shaking the cleanser bottle containing the one or more cleansers prior to pouring the portion of the one or more cleansers from the cleanser bottle.

In still another aspect, the method includes controlling the dosing of the one or more doses of the cleanser solution to be directed into a water port by a control unit. In one example, the control unit is connected to a control button positioned on a front end of the base seat of the toilet seat assembly of the wash system.

The wash system of the present invention is designed and adapted to apply a cleanser solution, skin protection lotions and oils, etc., directly to the skin and an operator of the wash system will be able to spray cleanser evenly on the individual, especially in hard-to-reach areas such as the bottom, back and neck of a human subject.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present invention includes a method and a wash-dry-clean-and-protect system for providing easy washing, cleaning and protection of a person's bottom while using a toilet is provided. In one embodiment, the wash-dry-clean-and-protect system can be placed directly over a rim of a toilet bowl or a seat of a toilet seat system. In another embodiment, the wash-dry-clean-and-protect system include a built-in cleanser assembly for the delivery of one or more cleansers and/or cleanser solutions, moisturizing creams, and/or skin sealant to a surface area of a human subject.

The built-in cleanser assembly as described herein is easy-to-handle and easy to dose and to be sprayed to the skin area of a person. The built-in cleanser assembly contains one or more cleanser containers for a cleanser (in a diluted solution or as a concentrate) to be poured from a cleanser bottle into one or more cleanser containers positioned inside a toilet seat assembly, as well as a sensor to allow for detecting the cleanser lever inside the cleanser container of the cleanser assembly and enable a user to easily operate and easily spray one or more doses of the cleanser onto a skin area of the user. The wash system with the built-in cleanser assembly can be handled automatically or functions together with a toilet seat or other devices. In one embodiment, a cleanser assembly is incorporated into a wash, clean and dry bidet system and is deigned to easily dispense water, cleaning solutions, moisturizing creams, skin sealant, etc., to a surface area of a human subject.

Figure 1:
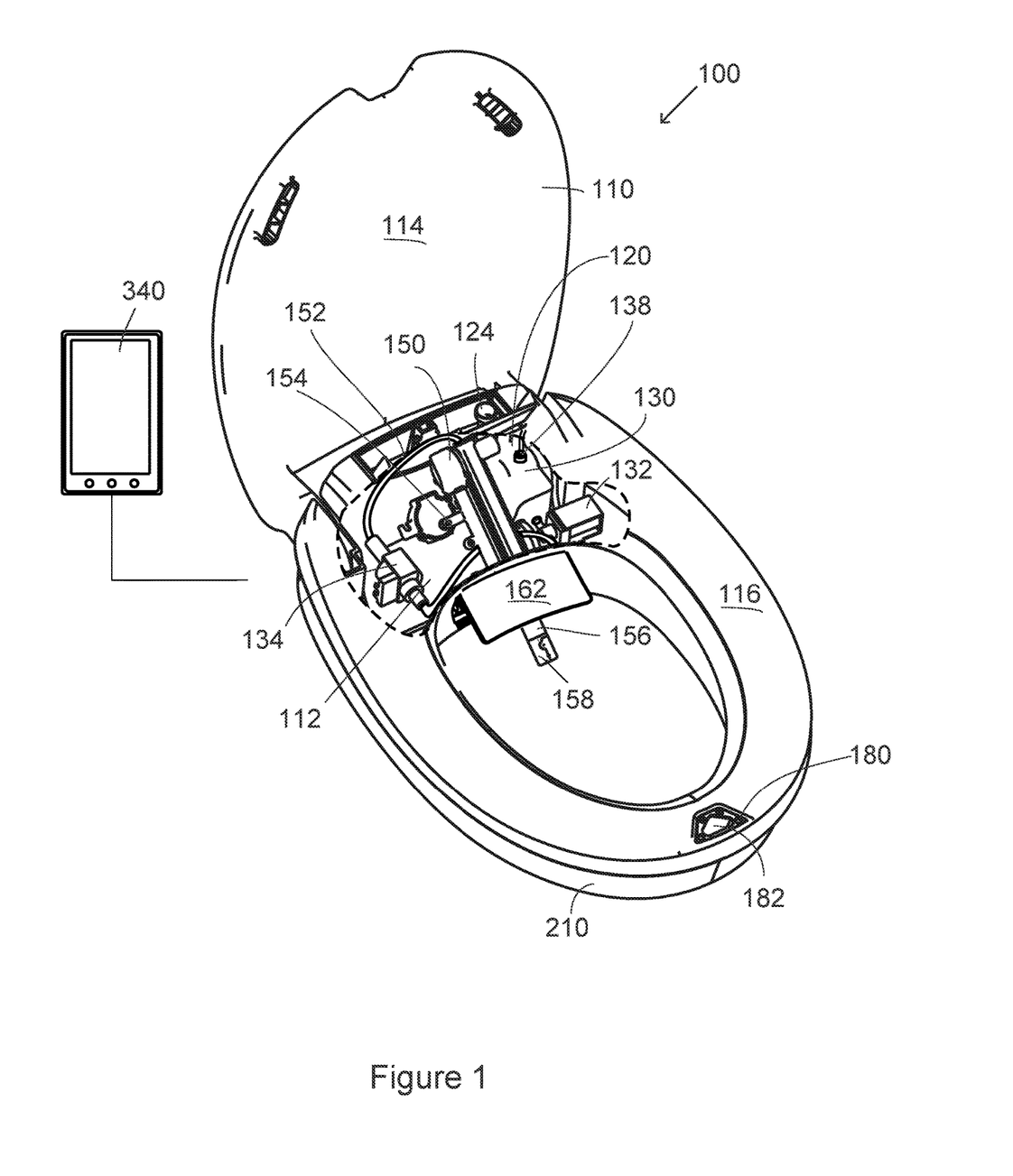
FIG. 1 is a perspective view of an exemplary wash system with a built-in cleanser assembly therein according to one embodiment of the invention.

FIG. 1 show one example of a wash system 100 with a toilet seat assembly 110 and a cleanser assembly 120 therein according to one embodiment of the invention. In one embodiment, the toilet seat assembly 110 includes a seat cover 114, a seat base 116, and a base housing 112 within the seat base 116. In another embodiment, the toilet seat assembly 110 further includes a nozzle cover 162 where nozzles of a nozzle spray assembly 150 can be extended in and out of a portion of the seat base 116 when the nozzle cover 162 is opened. The nozzle cover 162 is positioned on a side-wall of the base housing 112 of the seat base 116.

Figure 2:
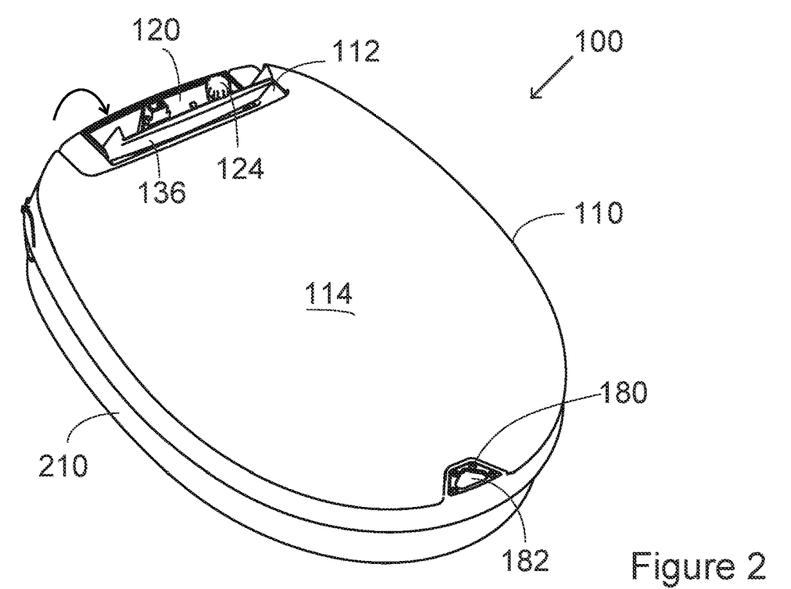
FIG. 2 is a top view of another exemplary wash system with a toilet seat assembly and a built-in cleanser assembly where a seat cover of the toilet seat assembly is in a seat-closed position (e.g., being laid down on top of a seat base) and positioned atop of the toilet seat assembly of the wash system, where a top cover of the built-in cleanser assembly is opened according to another embodiment of the invention.

In one example, the seat cover 114 is adapted to be put up over the seat base in a seat-open position (as shown in FIG. 1). In another example, the seat cover 114 is adapted to be laid down on top of the seat base 116 in a seat-close position (as shown in FIG. 2). Further, the toilet seat assembly 110 of the wash system 100 can be coupled atop to a conventional toilet, e.g., a toilet seat 210. As another example, the nozzle cover 162 is adapted to be in an open position ready for one or more nozzles (e.g., a water spray nozzle 156 as shown in FIG. 1) from the nozzle spray assembly 150 to extend out when the seat cover 114 is put up over the seat base 116 in the seat-open position.

The cleanser assembly 120 is positioned inside the base housing 112 of the toilet seat assembly 110 and is adapted to contain one or more cleanser containers 130 therein. The nozzle spray assembly 150 is connected to the one or more cleanser containers 130 of the cleanser assembly 120 inside the base housing 112 of the toilet seat assembly 110.

In one embodiment, wherein the cleanser assembly 120 is adapted to contain one or more cleanser containers 130 therein. In FIG. 1, the cleanser assembly 120 includes a cleanser container 130, a cleanser dosing valve 132, and a pump 134. The cleanser assembly 120 may also include a cleanser port 122 (shown in FIG. 6) having a first end 121, an opening 124 on its first end 121, a second end 123 where the one or more cleanser containers are connected to.

For example, the one or more cleanser containers 130 are adapted to contain one or more cleansers therein, and the opening 124 of the cleanser port 122 is used to receive the one or more cleansers to be poured into the cleanser container 130 via the opening 124 by a human user. Examples of the one or more cleansers include, but are not limited to, skin repair creams, skin protectants, skin extra protective creams (EPC), skin lotions, mild soaps, detergents, mild anti-bacterial soaps, and combinations thereof. One example of the cleanser is benzalkonium chloride.

As shown in FIG. 1, the cleanser dosing valve 132 is adapted to be connected to the one or more cleanser containers 130 to function together with the pump 134 adapted to pump one or more doses of the one or more cleansers from the cleanser dosing valve 132 to a water port 152 of the nozzle spray assembly 152 and form a cleaning solution therein ready to be sprayed out by the nozzle spray assembly 150.

In addition, the cleanser assembly 120 further includes a sensor 138 being positioned on a surface of the one or more cleanser containers 130 and adapted to detect a level of the one or more cleansers inside the one or more cleanser containers 130. In one example, one or more doses of the one or more cleansers within the one or more cleanser containers 130 are delivered from the cleanser assembly 120 via the water port 152 to the nozzle spray assembly 150 to be mixed with water into a cleanser solution ready to be sprayed out from a nozzle head of the nozzle spray assembly. For example, the nozzle spray assembly 150 may include a water spray nozzle 156 with a water spray nozzle head 158 such that the cleanser solution is sprayed out of the water spray nozzle head 158.

Figure 6:
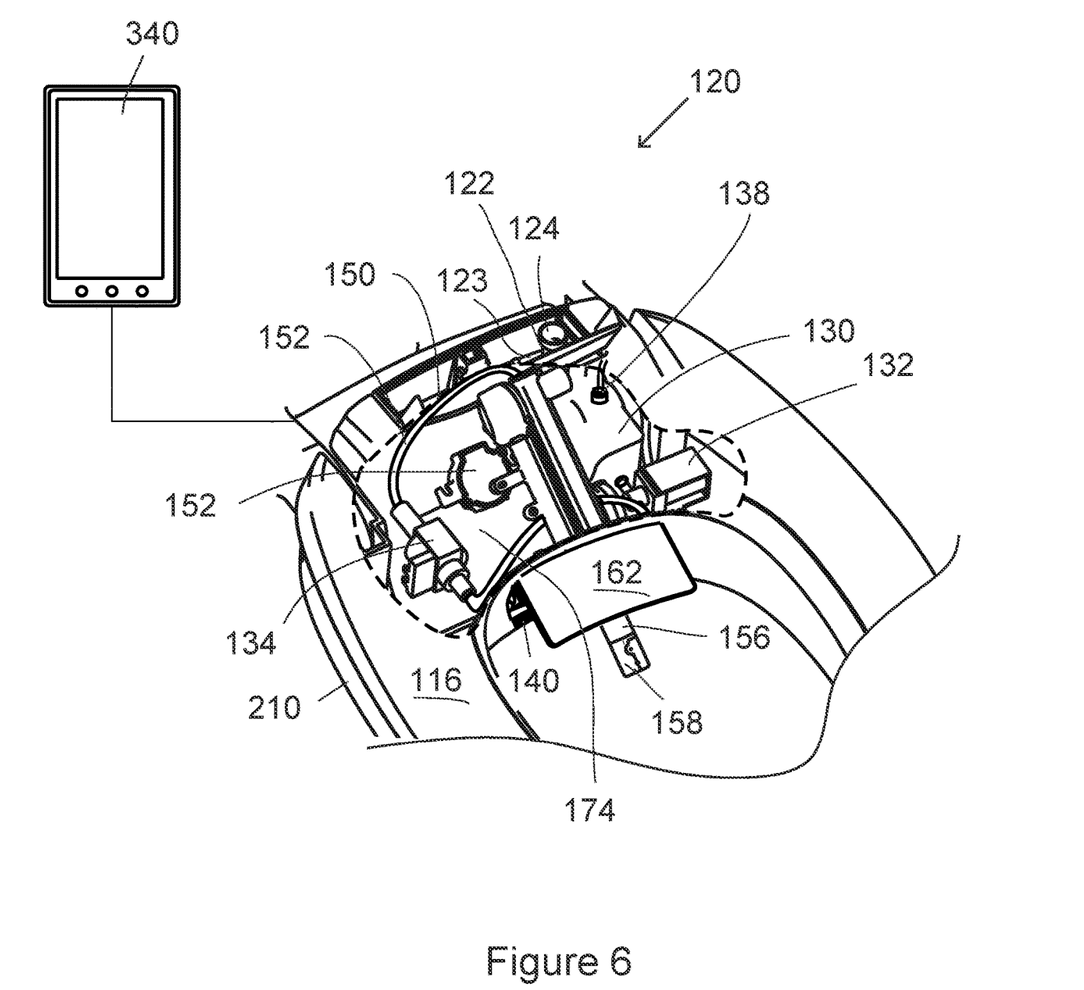
FIG. 6 is a detailed blown-up view of the cleanser assembly and the nozzle spray assembly of an exemplary wash system according to one embodiment of the invention.

In another embodiment, the wash system further includes a dryer assembly 140 (as shown in FIG. 6) with one or more fans, motors, and/or one or more retractable drying nozzle units adapted to deliver air at a predetermined temperature to a surface region of a human body. Each of one or more drying nozzle units of the drying nozzle assembly may include an air channel, a retractable element, a nozzle tip portion, and a drying nozzle opening.

In one example, the dryer assembly 140 may include a first driving motor being connected to the one or more drying nozzle units and adapted for moving the one or more retractable elements in retracting-and-extending motion. In addition, the drying nozzle assembly may further include a second driving motor being connected to the one or more drying nozzle unit and adapted for moving the one or more drying nozzle units in three-dimensional circular rotational motion. In one aspect, the fan of the drying nozzle assembly is adapted to blow air at an adjustable speed. In another aspect, wherein the fan of the drying nozzle assembly is adapted to blow air at an adjustable temperature.

Examples of a suitable toilet seat assembly 110, the nozzle spray assembly 150, and the dryer assembly 140 are also disclosed in the co-U.S. patent application Ser. No. 15/588,635, titled "A Seat and Cover System with Dynamic Spray Nozzle"; co-pending U.S. patent application Ser. No. 15/588,637, titled "Dynamic Drying Mechanism for a Wash and Clean System with"; co-pending U.S. patent application Ser. No. 15/588,638, titled "A seat and Cover System with Medicine Units"; co-pending U.S. patent application Ser. No. 15/588,640, titled "A Medicine Delivery, Wash, Clean and Air Dry System". The disclosure of all of these US patent applications is hereby incorporated by reference.

During operation or in idle position of the wash system 100, the seat cover 114 can be opened and positioned upward, such as being positioned against a water tank. The toilet seat assembly 110 includes a seat body with the seat base 116 facing upward so that a human subject can sit thereon. The seat cover 114 and the base seat 116 are formed to connect together, for example, using one or more hinges such that the seat cover 114 can be opened or closed over the seat base 116. The base housing 112 is contained within the seat base 114 to include the nozzle spray assembly therein. The base housing 112 is positioned near the back end of the seat base 114, and together with the seat base 116, they are used generally to house one or more assemblies (e.g., the spraying nozzle assembly 150, the dryer assembly 140, and/or a medicine delivery assembly, etc.) therein.

As shown in FIG. 1, one or more spray nozzles can be positioned inside the base housing 112 and can be adapted to be retractable and extendable out when the nozzle cover 162 is in an open position. The spray nozzles can also be, capable of moving in three dimensional rotational direction and in a horizontal plane. The spray nozzles or any suitable spray nozzle units positioned near the bottom of the seat base 116 can be adjusted to be retracted back into the base housing 116 so that the nozzle cover 162 can be in a close position.

In one embodiment, the function and operation of the wash system 100 is controlled by one or more control units (e.g., a control unit positioned adjacent to one side of the wash system 100, and/or a controlled unit 340, which can be positioned at a distance away from the bidet system in a wired or wireless fashion.

In one example, the wash system 100 is connected to the control unit 340 via Bluetooth or wireless connections so as to control the proper operation of the various components of the wash system 100. In one aspect, the wash system 100 includes a front end control element 180 positioned near a front end of the toilet seat assembly 110 for the control and operation of the wash system 100. The front end control element 180 may include a front end control button 182 adapted to be uses by a human subject.

The single button configuration may help ease the use and operations by a human subject, whereby only the front end control button 182 is sufficient to transmit electric signal and control the movements of various parts within the wash system 100. In one example, by pushing down the front end control button 182 once, an electric signal for directing the wash system 100 into a pre-set wash operation A or any other type of desirable full sequence operation can be transmitted to one or more control units within the wash system and control beginning and completion of the movements of the components of the wash system 100 for the pre-set operation. In another example, by pushing down the front end control button 182 twice consecutively or for any other desirable times, a different electric signal can be transmitted to one or more control units within the wash system to direct the wash system 100 into a different pre-set wash and operation B and control the movements of the components of the wash system 100 to execute the pre-set wash and operation B.

In FIG. 1, one control unit 340 and one front-end control element 180 are configured to function together, where the front end control element 180 is positioned to be on the front end of the seat base 116 to be closer for a user to touch the front end control button 182 and control the movements of the cleanser assembly 120 and the nozzle spray assembly 150 as well as the temperature and pressure of the spraying liquid spraying from one or more spray nozzles within the wash system 100. Alternatively, the control unit 340 may be a remote controlled unit being capable of communicating with the wash system 100.

The control unit 340 and the front-end control element 180 are configured to be communicating and directing one or more movements of the spraying nozzle assembly 150. The spray nozzle assembly 150 is adapted to include one or more spray nozzles to jet one or more solutions, such as water or any liquid, a cleaning solution, a barrier spray solution, a medicine-containing solution, and combinations thereof to a localized region (e.g., perianal region) of a human body private part.

In one example, the spray nozzle assembly 150 includes a water spray nozzle 156 having a water spray nozzle head on the front thereof and being adapted to move in a linear direction to be extended and retracted in and out of the nozzle cover 162. In another example, the spray nozzle assembly 150 is adapted to move in a vertical direction to move up and down (e.g., in a Z-direction or a gravitational direction), particularly after the spray nozzle assembly 150 has been extended out. In another example, the spray nozzle assembly 150 is adapted to move in a horizontal direction to move left-right (e.g., in a rocking motion), particularly after the spray nozzle assembly 150 are extended out.

The control unit 340 and the front-end control element 180 can cause the user to operate the wash system 100 reliably. The remote control units can provide "hands-free" options, therefore avoiding some discomfort or embarrassment from the user. For example, control units 340 can be mounted on the wall adjacent to or far away from the toilet. The control unit 340 has a screen and a keyboard with pushbuttons for turning the water or air on and off, for controlling the air temperature, etc. The water flow level may be selected by appropriate command through the remote control unit. The remote control unit is used to transmit appliance control data to the wash system 100. Inside the wash system 100, a decoder decodes the transmitted data. When the data is decoded, the wash system 100 responds to from an appliance control signal suitable for controlling the nozzle spray assembly 150 and other parts within the wash system 100. As another example, front-end control element 180 are installed on front end of the seat base 116. It enables a user to directly control the wash system 100 from the front side without having to turn sideways or turn around.

FIG. 2 shows a top view of the wash system 100 where a top cover 136 of the cleanser assembly 120 is closed. The top cover 136, as shown, may be positioned atop of the toilet seat assembly 110 near a top portion of the base housing 112 of the seat base 116 according to one embodiment of the invention. Alternatively, the top cover 136 can be positioned in any other positions close to the base housing 112 of the toilet seat assembly 110.

Figure 3A:
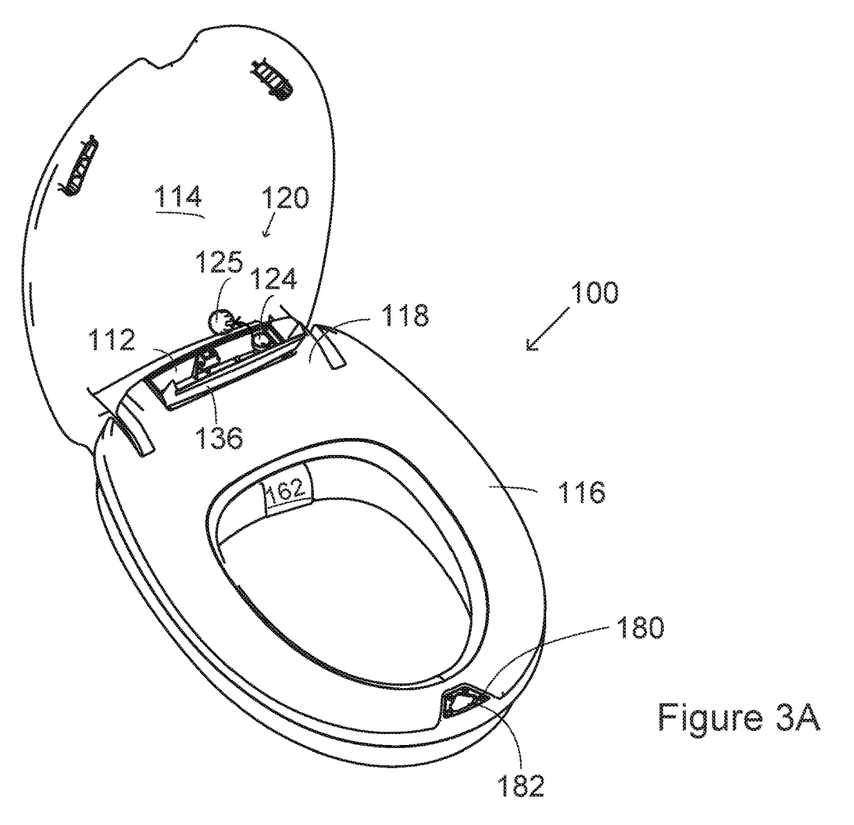
FIG. 3A is a perspective view of a toilet seat assembly of an exemplary wash system where a seat cover of the toilet seat assembly is in a seat-opened position (e.g., being put up over a seat base) and positioned over a base housing of the seat base within the wash system, a built-in cleanser assembly is positioned inside the base housing of the toilet seat assembly, where a top cover of the toilet seat assembly is opened on a top portion of the base housing according to another embodiment of the invention.
Figure 3B:
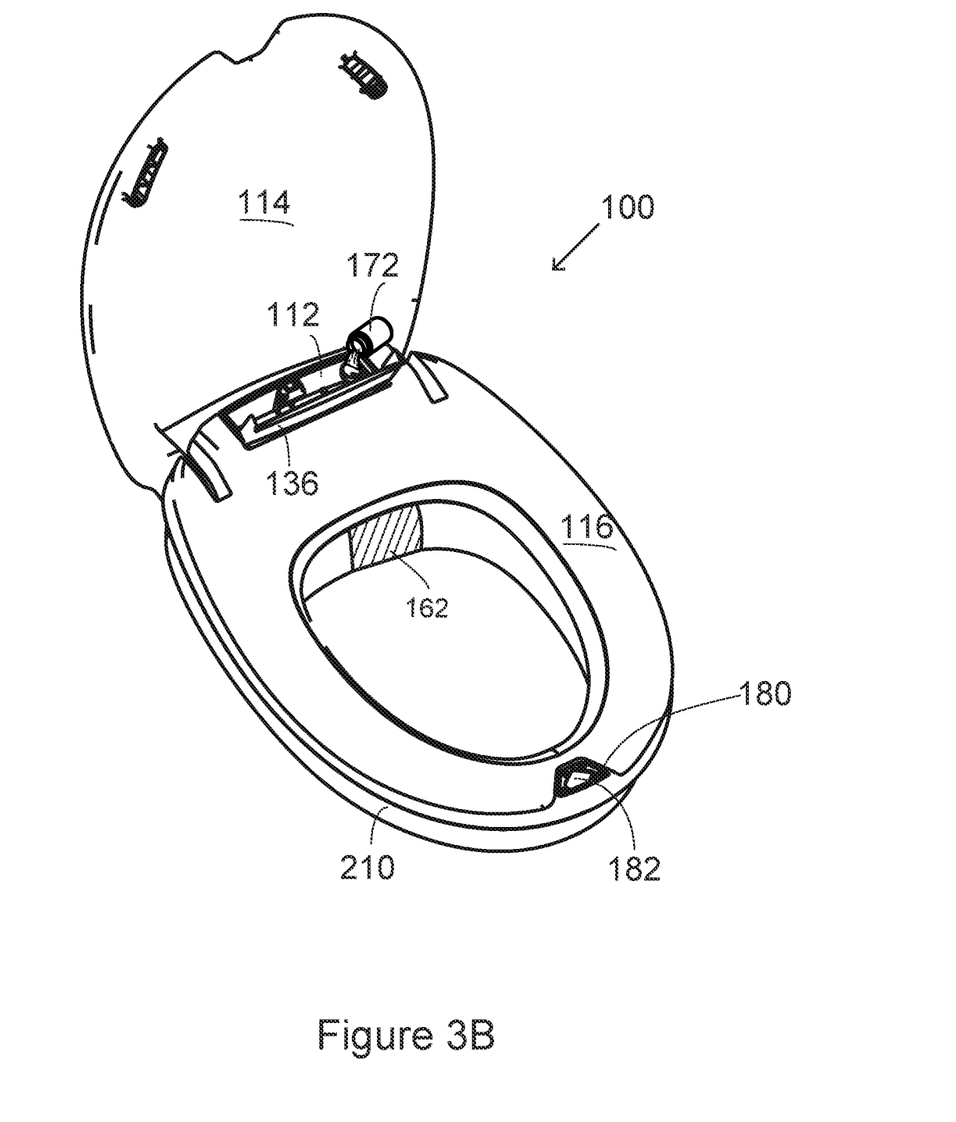
FIG. 3B is a perspective view of the wash system of the Example as shown in FIG. 3A, where a seat cover of the toilet seat assembly is opened and a top cover of the toilet seat assembly is opened as well so as to allow one or more cleansers from a cleanser bottle to be poured into an opening of a cleanser container of a cleanser assembly positioned inside a base housing of the seat base according to another embodiment of the invention.

In one aspect, the top cover 136 can be adapted to be opened when the seat cover 114 is put up over the seat base 116 in a seat-open position. In another aspect, the top cover 136 can be adapted to be closed when the seat cover 114 is put up over the seat base 116 in a seat-open position. In still other aspect, the top cover 136 is adapted to be opened when the seat cover 114 is laid down on top of the seat base 116 in a seat-close position. In a further aspect, the top cover 136 is adapted to be closed when the seat cover 114 is laid down on top of the seat base 116 in a seat-close position FIG. 3A shows on example of the toilet seat assembly 110 where the seat cover 114 of the toilet assembly 110 is opened, and the top cover 136 of the cleanser assembly 120 is also opened. The opening 124 of the cleanser port 122 may be closed by a cap 125. As shown in FIG. 3A, the cap 125 can be opened by a user prior to pouring a cleanser (either a concentrated or a diluted cleanser solution) from a cleanser bottle into the cleanser port 122 of the cleanser assembly 120. FIG. 3B shows the example of the wash system 100 as shown in FIG. 3A where one or more cleansers from a cleanser bottle 172 can be poured into the opening 124 of the cleanser port 122 (shown in FIG. 6) of the cleanser assembly 120 according to another embodiment of the invention.

In operation, the top cover 136 of the wash system 100 is opened by a human user, and then the cap 125 of the cleanser container 130 within the cleanser assembly 120 is also opened (such as by unscrewing the cap 125 to open the cap 125). Next, a portion of the one or more cleansers from the cleanser bottle 172 is poured into the cleanser container 130 of the cleanser assembly 120. Optionally, a human user may want to shake the cleanser bottle 172 containing the one or more cleansers prior to pouring the portion of the one or more cleansers from the cleanser bottle 172.

Figure 4A:
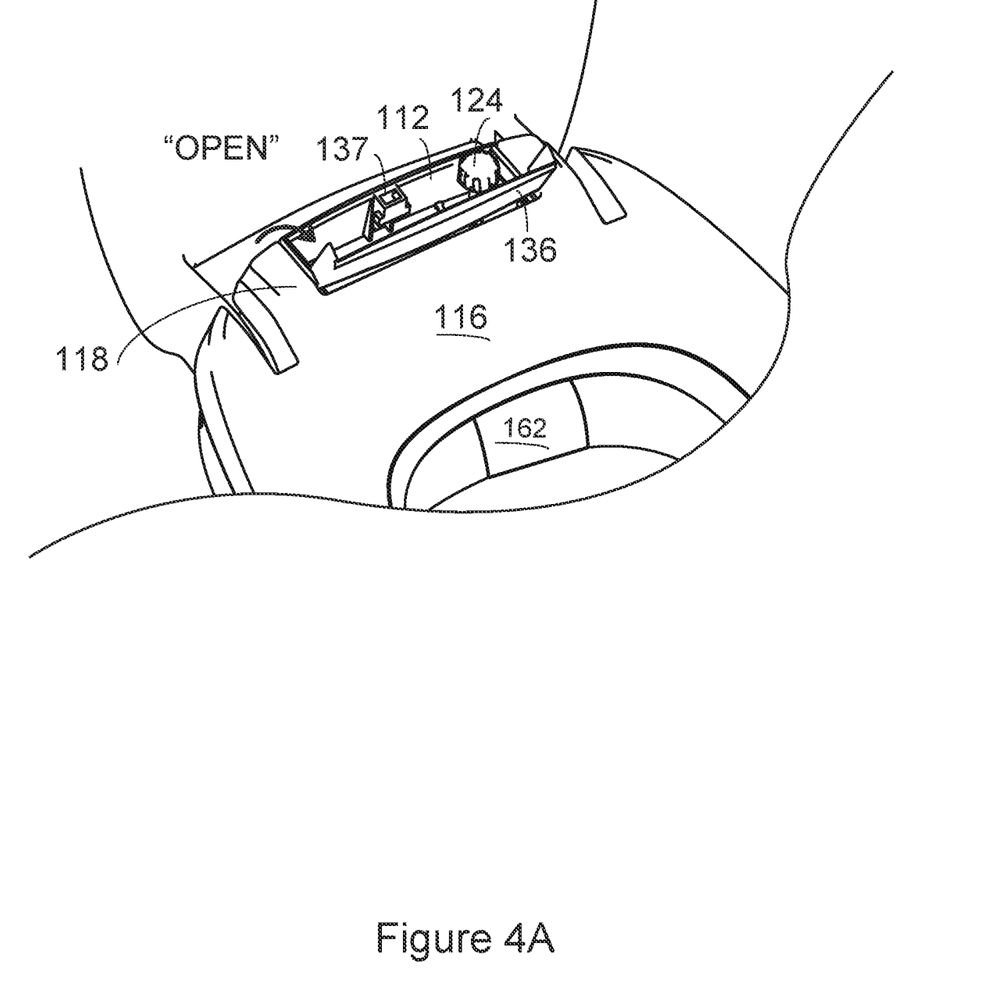
FIG. 4A is a blown-up view of a base housing of a toilet seat assembly of an exemplary wash system where a top cover of the toilet seat assembly is adapted to be opened to show a cap of a cleanser container within a built-in cleanser assembly positioned inside the base housing of the toilet seat assembly, according to another embodiment of the invention.

FIG. 4A is a blown-up view of the base housing 112 within the back end of the seat base 116 of the toilet seat assembly 110, where the top cover 136 is in an open position. The top cover 136, when is in a closed position, can be secured by a fixation means, such as a magnet 137. As shown in FIG. 4A, the cleanser container 130 of the cleanser assembly 120 is positioned inside the base housing 112 of the toilet seat assembly 110 and is capped by the cap 125 thereon.

Figure 4B:
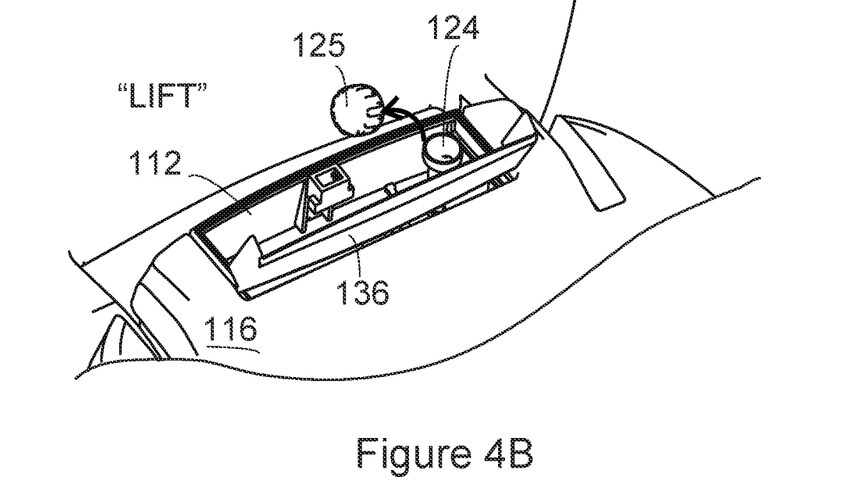
FIG. 4B is a blown-up view of the wash system of the Example as shown in FIG. 4A, where the top cover of the toilet seat assembly is opened and the cap of the cleanser container within the cleanser assembly is opened according to another embodiment of the invention.
Figure 4C:
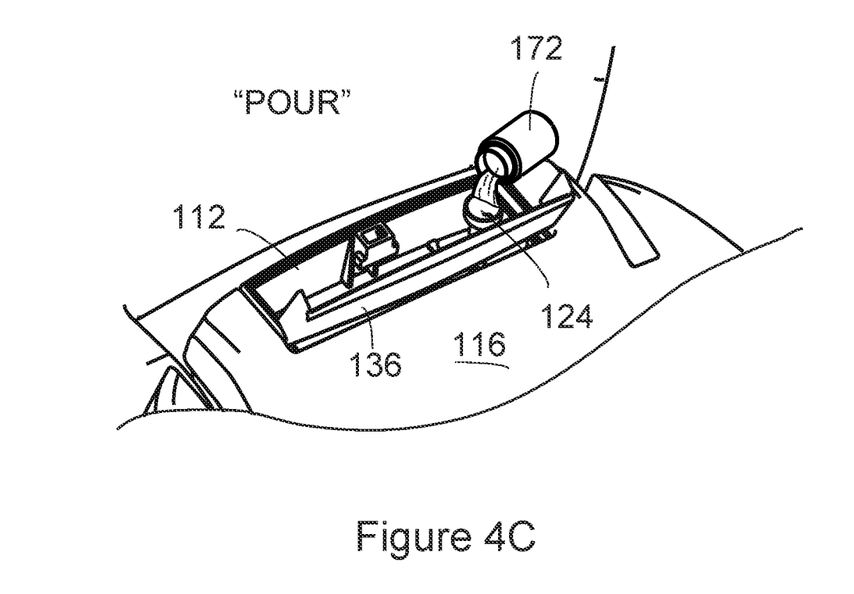
FIG. 4C is a blown-up view of the wash system of the Example as shown in FIG. 4B, one or more cleansers from a cleanser bottle is poured into an opening of the cleanser container positioned within the cleanser assembly inside the base housing of the toilet seat assembly according to another embodiment of the invention.

FIG. 4B is a blown-up top view of the base housing 112 of the wash system 100 as shown in FIG. 4A, where the top cover 136 of the toilet seat assembly 110 is opened and the cap 125 of the cleanser container 130 is lifted. FIG. 4C is a blown-up top view of the base housing 112, showing that one or more cleansers from the cleanser bottle 172 is poured into the opening 124 of the cleanser container 130 positioned within the cleanser assembly 120 inside the base housing 112 of the toilet seat assembly 110.

Figure 5:
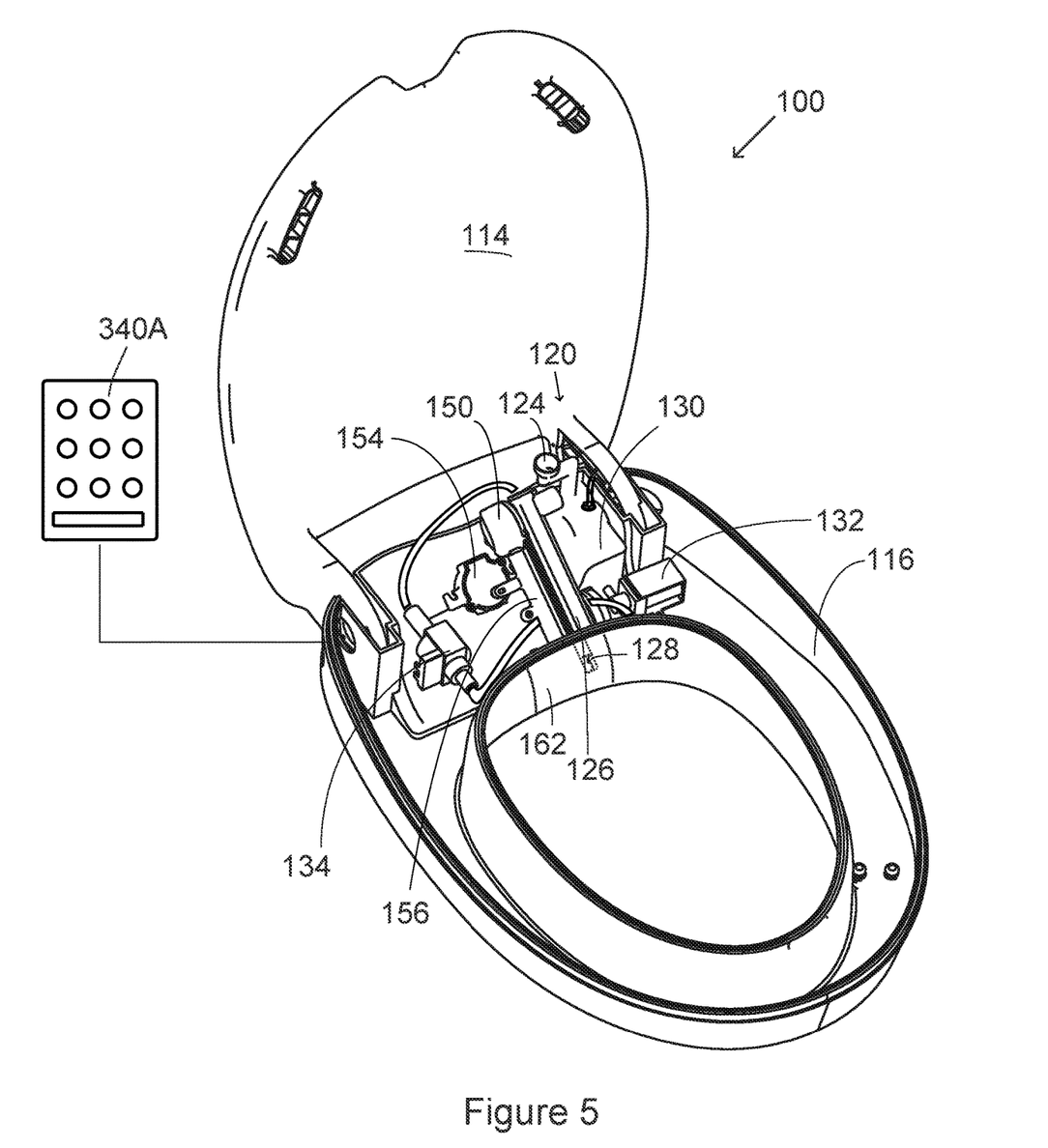
FIG. 5 is an inside view of a base housing of a toilet seat assembly of an exemplary wash system showing one example of a cleanser assembly and a nozzle spray assembly within the base housing of the wash system according to another embodiment of the invention.

FIG. 5 is another example of the base housing 112 of the toilet seat assembly 110 of the wash system 100. The cleanser assembly 110, the nozzle spray assembly 150, and/or the dryer assembly 140 can also be positioned within the base housing 112 of the wash system 100. As shown in FIG. 5, the nozzle spray assembly 150 may contain a cleanser spray nozzle 126 in addition to a water spray nozzle 156. The cleanser spray nozzle 126 may be used specifically for spraying a cleanser solution and the water spray nozzle 156 can be used for spraying water, and/or other solutions (e.g., a medicinal solution, a moisturizer solution, a lotion, oils, a barrier spray solution, mild soaps, detergents, mild anti-bacterial soaps, etc., among others). The cleanser spray nozzle 126 may include a cleanser spray nozzle head 128 positioned at its front end. In operation, as controlled by a control unit 340A, the water spray nozzle 126 retracted inside the nozzle cover 162 can be extended out of the nozzle cover 162 so that a cleanser solution may be sprayed out of the cleanser spray nozzle head 128. The nozzle spray assembly 150 may also contain one or more motors (e.g., the motor 154) to control the movements of the cleanser spray nozzle 126.

FIG. 6 is another example of a blown-up view of the cleanser assembly 120 and the nozzle spray assembly 150 of the wash system 100. The nozzle spray assembly 150 may contain the water spray nozzle 156 with the water spray nozzle head 158 positioned at its front end for spraying water and the cleanser solution that is being dosed to be sprayed out. In operation, the water spray nozzle 156 retracted inside the nozzle cover 162 can be extended out of the nozzle cover 162 so that water may be sprayed out of the water spray nozzle head 158. The nozzle spray assembly 150 may also contain one or more motors (e.g., motor 154) to control the movements of the water spray nozzle 156.

Additionally, the nozzle spray assembly 150 includes the water port 152 connected to the water spray nozzle 156 and a water hose (not shown) for delivering water into the water spray nozzle 156. In one embodiment, the water port 152 is also connected to the cleanser assembly 120. For example, the pump 134 of the cleanser assembly 120 can be used to pump one or more cleansers delivered from the cleanser container 130 via the cleanser dosing valve 132 into the water port 152. In one embodiment, the cleanser dosing valve 132 and the pump 134 functions together to control and dose one or more doses of the cleanser contained inside the cleanser container 130 and delivered into the nozzle spray assembly 150 of the wash system 100.

In one example, the cleanser can be mixed into the water port 152 and being sprayed out of the water spray nozzle head 158 of the water spray nozzle 156. In another example, the cleanser can be mixed into a separate cleanser port and being sprayed out of a cleanser spray nozzle head 128 of a cleanser spray nozzle 126, as shown in FIG. 5. In one embodiment, the nozzles (e.g., the water spray nozzle 156, the cleanser spray nozzle 126, etc.) of the nozzle spray assembly 150 are adapted to move back and forth, sideway, rockingly and/or rotatably in three-dimensional direction.

As shown in FIG. 6, the wash system 100 may further include a dryer assembly 140. In another example, the dryer assembly 140 and the nozzle spray assembly 150 are combined and formed into a dynamic dryer and spray nozzle assembly, such as the nozzle spray assembly as shown in FIGS. 5-6. In one aspect, the dynamic dryer and spray nozzle assembly is able to move back and forth, sideway, and/or rotatably in three-dimensional direction.

The wash and dry system of the present invention applies water and cleansers, skin protection lotions and oils, directly to the skin and an operator of the wash and dry system will be able to spray lotions evenly on the individual, especially in hard-to-reach areas such as the bottom, back and neck of a human subject. Example of the one or more cleansers include skin repair creams, skin protectants, skin extra protective creams (EPC), skin lotions, mild soaps, detergents, mild anti-bacterial soaps, and combinations thereof. In one example, the cleansers comprise benzalkonium chloride.

In addition, the wash and dry system may further include a power switch, a power indicator for powering up the system and operating wash, clean, dry, protect, and/or other functions of the system. In one aspect, the system is connected to a power cord. In another aspect, the system is connected to a battery power pack.

Figure 7:
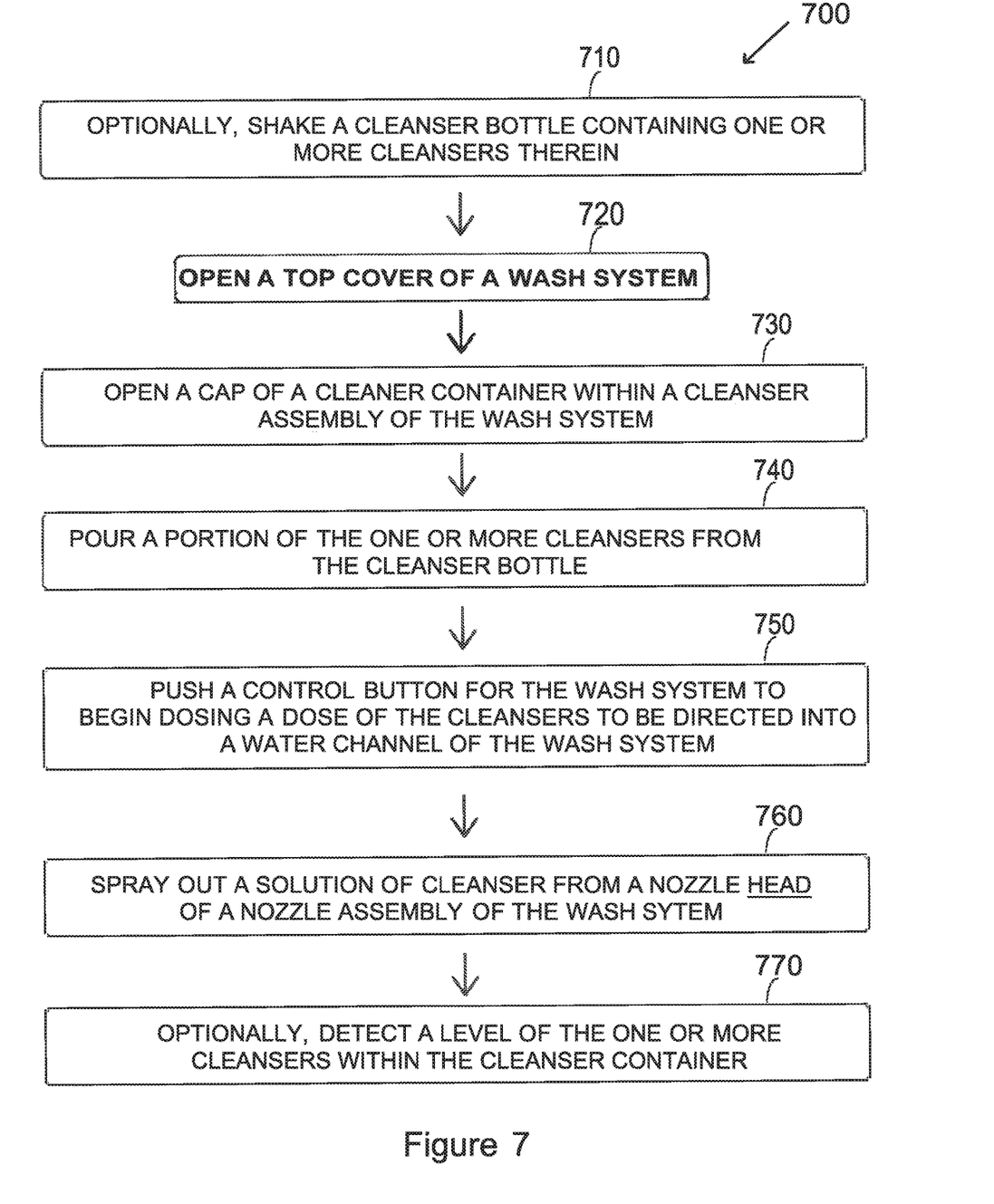
FIG. 7 illustrates a method of operating a wash system with a built-in cleanser assembly inside a base housing of a toilet seat assembly according to one or more embodiments of the invention.

FIG. 7 illustrates a method 700 of operating a wash system 100 which contains the cleanser assembly 120 according to one or more embodiments of the invention. The method may include a step 720 of opening a top cover of a cleanser assembly of a wash system, and a step 730 of opening a cap of a cleanser container within a cleanser assembly of the wash system. Optionally, at step 710, the cleanser bottle containing one or more cleansers is shaken prior to be poured into the cleanser port of the cleanser assembly.

At step 740, a portion of the one or more cleansers from the cleanser bottle containing one or more cleansers is poured into an opening of a cleanser port of the cleanser assembly. At step 750, a user can push one or more control buttons (e.g., the front-end control button 182 of the front-end control element 180) or touch a control screen of a control unit (e.g., the control unit 340, 340A) so that the wash system can begin to operate and start to dose one or more doses of the cleanser into a water channel (e.g., the water port 152, or other cleanser channels) connected to a nozzle spray assembly of the wash system.

Next, at step 760, a solution of cleanser can be sprayed out from a nozzle head (e.g., the water spray nozzle head 158 and the cleanser spray nozzle head 128, etc.) of a nozzle spray assembly of the wash system. Preferably, amount of the cleanser solution is dosed and controlled (e.g., controlled by the cleanser dosing valve 132)

Optionally, at step 760, a level of the cleanser within the cleanser container is detected by a sensor (e.g., by the sensor 136) such that if the level of the cleanser within the cleanser container 130 is too low, there is an indicator signal, a warning sign, or a warning sound can be generated. A user may need to add and pour more concentrated cleanser from a cleanser bottle into the cleanser container within the cleanser assembly of the wash system.

In general, one or more doses of a cleanser can be directed into a water channel of the wash system, and spraying out a solution of the cleanser from a nozzle head of a nozzle spray assembly of the wash system, where the wash system includes a toilet seat assembly, a cleanser assembly inside a housing of the toilet seat assembly and the cleanser assembly being adapted to contain the cleanser therein, and a nozzle spray assembly connected to the cleanser assembly inside the housing of the toilet seat assembly. In one aspect, the method also includes washing and cleansing a surface area of the human subject using the solution being sprayed out of the nozzle head of the nozzle spray assembly, and/or drying a surface area of the human subject using a dryer assembly of the wash system.

In still another aspect, the method includes controlling the dosing of the one or more doses of the cleanser to be directed into the water channel by a control unit. In one example, the control unit is connected to a control button positioned on the toilet seat assembly of the wash system The wash system of the present invention is designed and adapted to apply a cleanser solution, skin protection lotions and oils, etc., directly to the skin and an operator of the wash system will be able to spray cleanser evenly on the individual, especially in hard-to-reach areas such as the bottom, back and neck of a human subject.

While the foregoing is directed to embodiments of the present invention, other and further embodiments of the invention may be devised without departing from the basic scope thereof, and the scope thereof is determined by the claims that follow.

The invention claimed is:

1. A wash system, comprising:
   a toilet seat assembly including a seat cover and a seat base, the seat base including a base housing;
   a cleanser assembly positioned inside the base housing, the cleanser assembly including one or more cleanser containers, each cleanser container configured to contain a liquid cleanser therein;
   a nozzle spray assembly fluidically connected to the one or more cleanser containers of the cleanser assembly, the nozzle spray assembly configured to be moved between a retracted position and an extended position to deliver the liquid cleanser to a perineal region of a user; and
   a control unit positioned on a front end of the seat base, the control unit configured to receive a user input and further configured to control an amount of the liquid cleanser to deliver to the perineal region of the user based at least in part on the user input;
   wherein the control unit is configured to cause the nozzle spray assembly to operate in a selected one of a plurality of pre-set wash operations, each of the plurality of pre-set wash operations corresponding to, and configured to be selected based on, a different number of times the control unit is actuated by the user.

2. The wash system of claim 1, further comprising a dryer assembly.

3. The wash system of claim 1, further comprising a top cover positioned on the base housing of the seat base, the top cover configured to cover an opening of the cleanser assembly, wherein the opening permits access to the one or more cleanser containers.

4. The wash system of claim 1, further comprising a nozzle cover positioned on a side-wall of the base housing, the nozzle cover configured to cover the nozzle spray assembly when the nozzle spray assembly is in the retracted position.

5. The wash system of claim 1, wherein the cleanser assembly further comprises a sensor positioned on a surface of the one or more cleanser containers, the sensor configured to detect a level of the liquid cleanser inside the one or more cleanser containers.

6. The wash system of claim 1, wherein the control unit is configured to control a pump to deliver one or more doses of the liquid cleanser contained within the one or more cleanser containers to the nozzle spray assembly to be mixed with water to form a cleanser solution.

7. The wash system of claim 6, wherein the nozzle spray assembly comprises a water spray nozzle with a water spray nozzle head, and wherein the cleanser solution is sprayed out of the water spray nozzle head.

8. The wash system of claim 6, wherein the nozzle spray assembly comprises a cleanser spray nozzle and a water spray nozzle, and wherein the cleanser solution is sprayed out of a cleanser spray nozzle head of the cleanser spray nozzle and water is sprayed out of a water spray nozzle head of the water spray nozzle.

9. The wash system of claim 1, wherein the liquid cleanser comprises one or a combination of skin repair creams, skin protectants, skin extra protective creams (EPC), skin lotions, mild soaps, detergents, mild anti-bacterial soaps, and benzalkonium chloride.

10. A kit comprising:
    the wash system of claim 1; and
    a refill container having additional liquid cleanser stored therein for refilling the one or more cleanser containers of the cleanser assembly.

11. The wash system of claim 1, wherein the control unit is configured to adjust the temperature of the liquid cleanser based at least in part on the user input.

12. The wash system of claim 1, wherein the control unit comprises a button configured to be actuated by the user.

13. A wash system, comprising:
    a toilet seat assembly including a seat cover, a seat base, and a base housing, wherein the seat cover is configured to be moved between a closed position and an open position;
    a cleanser assembly positioned inside the base housing of the toilet seat assembly, the cleanser assembly including one or more cleanser containers positioned in the base housing of the toilet seat assembly, wherein each of the one or more cleanser containers are adapted to contain a liquid cleanser therein; and
    a cleanser port positioned inside the base housing, the cleanser port including a first end having an opening thereon; and a second end fluidically connected to the one or more cleanser containers;
    a nozzle spray assembly fluidically connected to the one or more cleanser containers of the cleanser assembly, the nozzle spray assembly configured to be moved between a retracted position and an extended position to deliver the liquid cleanser to a perineal region of a user; and
    a control unit positioned on a front end of the seat base, the control unit configured to receive a user input and further configured to control an amount of the liquid cleanser to deliver to the perineal region of the user based at least in part on the user input;

wherein the control unit is configured to cause the nozzle spray assembly to operate in a selected one of a plurality of pre-set wash operations, each of the plurality of pre-set wash operations corresponding to, and configured to be selected based on, a different number of times the control unit is actuated by the user.

14. The wash system of claim 13, wherein the cleanser assembly further includes a cleanser dosing valve coupled to the one or more cleanser containers; and wherein a pump is configured to pump a dose of the liquid cleanser from the cleanser dosing valve to a water port of the nozzle spray assembly upon the control unit receiving the user input.

15. The wash system of claim 13, wherein the liquid cleanser comprises one or a combination of skin repair creams, skin protectants, skin extra protective creams (EPC), skin lotions, mild soaps, detergents, mild anti-bacterial soaps, and benzalkonium chloride.

16. The wash system of claim 13, wherein the cleanser assembly further includes a pump, the pump configured to deliver one or more doses of the liquid cleanser within the one or more cleanser containers to the nozzle spray assembly to be mixed with water to form a cleanser solution.

17. The wash system of claim 16, wherein the nozzle spray assembly comprises a water spray nozzle with a water spray nozzle head, and wherein the cleanser solution is sprayed out of the water spray nozzle head.

18. The wash system of claim 13, wherein the control unit comprises a button configured to be actuated by the user.

* * * * *